US011453880B2

(12) United States Patent
Morishita et al.

(10) Patent No.: US 11,453,880 B2
(45) Date of Patent: Sep. 27, 2022

(54) CHIMERIC DECOY

(71) Applicants: AnGes, Inc., Ibaraki (JP); GeneDesign, Inc., Ibaraki (JP)

(72) Inventors: Ryuichi Morishita, Suita (JP); Takashi Miyake, Suita (JP); Tetsuo Miyake, Suita (JP); Takahiro Nakazawa, Ibaraki (JP); Makoto Sakaguchi, Ibaraki (JP); Satoshi Inoue, Ibaraki (JP); Ryoji Ueki, Ibaraki (JP)

(73) Assignees: ANGES, INC., Ibaraki (JP); GENEDESIGN, INC., Ibaraki (JP)

( * ) Notice: Subject to any disclaimer, the term of this patent is extended or adjusted under 35 U.S.C. 154(b) by 275 days.

(21) Appl. No.: 15/758,584

(22) PCT Filed: Sep. 9, 2016

(86) PCT No.: PCT/JP2016/076659
§ 371 (c)(1),
(2) Date: Apr. 19, 2018

(87) PCT Pub. No.: WO2017/043639
PCT Pub. Date: Mar. 16, 2017

(65) Prior Publication Data
US 2018/0298381 A1    Oct. 18, 2018

(30) Foreign Application Priority Data
Sep. 9, 2015  (JP) .............................. JP2015-177341

(51) Int. Cl.
C12N 15/113 (2010.01)
C12N 15/09 (2006.01)
(52) U.S. Cl.
CPC ............ *C12N 15/113* (2013.01); *C12N 15/09* (2013.01); *C12N 2310/13* (2013.01); *C12N 2310/353* (2013.01)
(58) Field of Classification Search
CPC .......................... C12N 2310/13; A61K 47/593
See application file for complete search history.

(56) References Cited

U.S. PATENT DOCUMENTS

| | | | | |
|---|---|---|---|---|
| 7,943,591 B2* | 5/2011 | Mamet | ..................... | A61P 25/04 514/44 R |
| 2006/0154886 A1* | 7/2006 | Weihe | ................... | C07K 14/705 514/44 R |
| 2007/0014840 A1 | 1/2007 | Lee et al. | | |
| 2014/0314864 A1* | 10/2014 | Cheng | ................. | A61K 47/549 424/497 |

FOREIGN PATENT DOCUMENTS

| | | |
|---|---|---|
| EP | 1 803 811 A1 | 7/2007 |
| JP | 2010-90103 A | 4/2010 |
| JP | 2011-32269 A | 2/2011 |
| JP | 2014-37358 A | 2/2014 |
| WO | WO 2008/141308 A2 | 11/2008 |

OTHER PUBLICATIONS

Bennett et al. Interleukin-4 suppression of tumor necrosis factor alpha-stimulated E-selectin gene transcription is mediated by STAT6 antagonism of NF-KB. The Journal of Biological Chemistry, vol. 272, No. 15, pp. 10212-10219, 1997. (Year: 1997).*
Galang et al. Oncogenic Ras can induce transcriptional activation through a variety of promoter elements, including tandem c-Ets-2 binding sites. Oncogene, vol. 9, No. 10, pp. 2913-2921, 1994. (Year: 1994).*
Wasylyk et al. The c-Ets oncoprotein activates the stromelysin promoter through the same elements as several non-nuclear oncoproteins. The EMBO Journal, vol. 10, No. 5, pp. 1127-1134, 1991. (Year: 1991).*
Clark et al., "Knockdown of TNFR1 by the sense strand of an ICAM-1 siRNA: dissection of an off-target effect," Nucleic Acids Research (2008), vol. 36, No. 4, pp. 1081-1097.
English translation of International Preliminary Report on Patentability and Written Opinion dated Mar. 22, 2018, in PCT International Application No. PCT/JP2016/076659 (Forms PCT/IB/326, PCT/IB/373, and PCT/ISA/237).
International Search Report dated Nov. 22, 2016, in PCT International Application No. PCT/JP2016/076659.
Miyake, T. and R. Morishita, "Kakusan Iyaku o Mochiita Ketsueki Shikkan ni Taisuru Bunshi Chiryoho," Folia Pharmacol. Japan (2007), vol. 129, pp. 158-162, with English abstract.
Morishita, R., "Innovation of decoy toward to real drugs," Journal of Clinical and Experimental Medicine (Jul. 30, 2011), vol. 238, No. 5, pp. 529-535, with English abstract.

* cited by examiner

*Primary Examiner* — Jennifer Dunston
(74) *Attorney, Agent, or Firm* — Birch, Stewart, Kolasch & Birch, LLP

(57) ABSTRACT

Disclosed is a double-stranded oligonucleotide decoy including two transcription factor-binding sites, while keeping its size small. The double-stranded oligonucleotide decoy showing binding affinities for two transcription factors includes a first binding site for a first transcription factor and a second binding site for a second transcription factor. A first strand including the sense strand of the first binding site and a second strand including the sense strand of the second binding site are hybridized to form a double strand in which the sense strand of the first binding site and the sense strand of the second binding site are at least partly hybridized.

9 Claims, 7 Drawing Sheets
Specification includes a Sequence Listing.

Amount of histamine in lung tissue

SEQUENCE LISTING

<160> NUMBER OF SEQ ID NOS: 27

<210> SEQ ID NO 1
<211> LENGTH: 15
<212> TYPE: DNA
<213> ORGANISM: Artificial Sequence
<220> FEATURE:
<223> OTHER INFORMATION: Synthetic: chimera decoy NF-kappaB/STAT6-15mer-B

<400> SEQUENCE: 1
gggatttcct gggaa                                               15

<210> SEQ ID NO 2
<211> LENGTH: 10
<212> TYPE: DNA
<213> ORGANISM: Artificial Sequence
<220> FEATURE:
<223> OTHER INFORMATION: Synthetic: binding region of NF-kappaB

<400> SEQUENCE: 2
gggatttcct                                                     10

<210> SEQ ID NO 3
<211> LENGTH: 11
<212> TYPE: DNA
<213> ORGANISM: Artificial Sequence
<220> FEATURE:
<223> OTHER INFORMATION: Synthetic: binding region of STAT6

<400> SEQUENCE: 3
ttcccaggaa a                                                   11

<210> SEQ ID NO 4
<211> LENGTH: 10
<212> TYPE: DNA
<213> ORGANISM: Artificial Sequence
<220> FEATURE:
<223> OTHER INFORMATION: Synthetic: consensus sequence of NF-kappaB

<400> SEQUENCE: 4 gggrhtyyhc                                                     10

<210> SEQ ID NO 5
<211> LENGTH: 10
<212> TYPE: DNA
<213> ORGANISM: Artificial Sequence
<220> FEATURE:
<223> OTHER INFORMATION: Synthetic: consensus sequence of STAT6
<220> FEATURE:
<221> NAME/KEY: misc_feature
<222> LOCATION: (4)..(7)
<223> OTHER INFORMATION: n is a, c, g, or t

<400> SEQUENCE: 5 ttcnnnngaa                                                     10

<210> SEQ ID NO 6
<211> LENGTH: 15
<212> TYPE: DNA
<213> ORGANISM: Artificial Sequence
<220> FEATURE:
<223> OTHER INFORMATION: Synthetic: chimera decoy NF-kappaB/STAT6-15mer-A

<400> SEQUENCE: 6
gggacttccc atgaa                                               15

<210> SEQ ID NO 7
<211> LENGTH: 15
<212> TYPE: DNA
<213> ORGANISM: Artificial Sequence
<220> FEATURE:
<223> OTHER INFORMATION: Synthetic: chimera decoy NF-kappaB/Ets1-15mer-A

<400> SEQUENCE: 7
ggggacttcc tgctc                                                15

<210> SEQ ID NO 8
<211> LENGTH: 15
<212> TYPE: DNA
<213> ORGANISM: Artificial Sequence
<220> FEATURE:
<223> OTHER INFORMATION: Synthetic: chimera decoy NF-kappaB/Ets1-15mer-B

<400> SEQUENCE: 8
ggggacttcc gggtg                                                15

<210> SEQ ID NO 9
<211> LENGTH: 15
<212> TYPE: DNA
<213> ORGANISM: Artificial Sequence
<220> FEATURE:
<223> OTHER INFORMATION: Synthetic: chimera decoy NF-kappaB/NF-AT-
      15mer-A

<400> SEQUENCE: 9
ggggaatttt cctct                                                15

<210> SEQ ID NO 10
<211> LENGTH: 15
<212> TYPE: DNA
<213> ORGANISM: Artificial Sequence
<220> FEATURE:
<223> OTHER INFORMATION: Synthetic: chimera decoy NF-kappaB/NF-AT-
      15mer-B

<400> SEQUENCE: 10
gggggatttt cctct                                                15

<210> SEQ ID NO 11
<211> LENGTH: 15
<212> TYPE: DNA
<213> ORGANISM: Artificial Sequence
<220> FEATURE:
<223> OTHER INFORMATION: Synthetic: chimera decoy NF-kappaB/STAT1-
      15mer-A

<400> SEQUENCE: 11
gggacttcca ggaat                                                15

<210> SEQ ID NO 12
<211> LENGTH: 15
<212> TYPE: DNA
<213> ORGANISM: Artificial Sequence
<220> FEATURE:
<223> OTHER INFORMATION: Synthetic: chimera decoy NF-kappaB/STAT1-
      15mer-B

<400> SEQUENCE: 12
gggacttccc ggaat                                                15

<210> SEQ ID NO 13

```
<211> LENGTH: 15
<212> TYPE: DNA
<213> ORGANISM: Artificial Sequence
<220> FEATURE:
<223> OTHER INFORMATION: Synthetic: chimera decoy NF-kappaB/NF-IL6-
      15mer-A

<400> SEQUENCE: 13
gggatttccc aatct                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic: chimera decoy NF-kappaB/NF-IL6-
      15mer-B

<400> SEQUENCE: 14
gggattccgc aatct                                                    15

<210> SEQ ID NO 15
<211> LENGTH: 13
<212> TYPE: DNA
<213> ORGANISM: Artificial Sequence
<220> FEATURE:
<223> OTHER INFORMATION: Synthetic: known NF-kappaB decoy

<400> SEQUENCE: 15
aggggatttc ccc                                                      13

<210> SEQ ID NO 16
<211> LENGTH: 15
<212> TYPE: DNA
<213> ORGANISM: Artificial Sequence
<220> FEATURE:
<223> OTHER INFORMATION: Synthetic

<400> SEQUENCE: 16
ttcccaggaa atccc                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic

<400> SEQUENCE: 17
ttcatgggaa gtccc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18
gagcaggaag tcccc                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 19
cacccggaag tcccc                                                15

<210> SEQ ID NO 20
<211> LENGTH: 15
<212> TYPE: DNA
<213> ORGANISM: Artificial Sequence
<220> FEATURE:
<223> OTHER INFORMATION: Synthetic

<400> SEQUENCE: 20
agaggaaaat tcccc                                                15

<210> SEQ ID NO 21
<211> LENGTH: 15
<212> TYPE: DNA
<213> ORGANISM: Artificial Sequence
<220> FEATURE:
<223> OTHER INFORMATION: Synthetic

<400> SEQUENCE: 21
agaggaaaat ccccc                                                15

<210> SEQ ID NO 22
<211> LENGTH: 15
<212> TYPE: DNA
<213> ORGANISM: Artificial Sequence
<220> FEATURE:
<223> OTHER INFORMATION: Synthetic

<400> SEQUENCE: 22
attcctggaa gtccc                                                15

<210> SEQ ID NO 23
<211> LENGTH: 15
<212> TYPE: DNA
<213> ORGANISM: Artificial Sequence
<220> FEATURE:
<223> OTHER INFORMATION: Synthetic

<400> SEQUENCE: 23
attccgggaa gtccc                                                15

<210> SEQ ID NO 24
<211> LENGTH: 15
<212> TYPE: DNA
<213> ORGANISM: Artificial Sequence
<220> FEATURE:
<223> OTHER INFORMATION: Synthetic

<400> SEQUENCE: 24
agattgggaa atccc                                                15

<210> SEQ ID NO 25
<211> LENGTH: 15
<212> TYPE: DNA
<213> ORGANISM: Artificial Sequence
<220> FEATURE:
<223> OTHER INFORMATION: Synthetic

<400> SEQUENCE: 25
agattgggaa atccc                                                15

<210> SEQ ID NO 26
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 26
ccttgaaggg atttccctcc                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gtatttccca gaaaaggaac                                                  20
```

CHIMERIC DECOY

TECHNICAL FIELD

The present invention relates to a double-stranded oligonucleotide decoy (hereinafter also referred to as "chimeric decoy") showing binding affinities for two transcription factors.

REFERENCE TO SEQUENCE LISTING SUBMITTED VIA EFS-WEB

This application includes an electronically submitted sequence listing in .txt format. The .txt file contains a sequence listing entitled "2020-06-30_0760-0487PUS1_ST25.txt" created on Jun. 20, 2020 and is size 5,858 bytes in size. The sequence listing contained in this .txt file is part of the specification and is hereby incorporated by reference herein in its entirety.

BACKGROUND ART

Various double-stranded oligonucleotide decoys showing a binding affinity for a transcription factor are known (e.g., Patent Document 1). It is known to treat or prevent diseases caused by a transcription factor by administering a decoy for the transcription factor to reduce the activity of the transcription factor of interest. The word "decoy" means "decoy" in English and refers to those having a structure that resembles one to which a certain substance should originally bind or act. A decoy mainly used for a transcription factor is a double-stranded oligonucleotide having the same DNA sequence as the binding region of the transcription factor on the genome gene. In the presence of a decoy composed of such an oligonucleotide, some of the transcription factor molecules bind to the decoy oligonucleotide, instead of binding to the binding region on the genomic gene to which it should have bound. This results in a decrease in the number of transcription factor molecules that bind to the binding region on the genomic gene to which it should have bound, leading to a decrease in the activity of the transcription factor. In this case, the oligonucleotide acts as a fake (decoy) of the real binding region on the genomic gene and binds with the transcription factor. Therefore, the oligonucleotide is called decoy.

Various double-stranded oligonucleotide decoys showing inhibitory activities to a plurality of different transcription factors are known (e.g., Patent Document 2). Administration of such a decoy provides simultaneous inhibition of activities of the plurality of different transcription factors, which may be advantageous for treatment or prevention of diseases. For example, Patent Document 2 discloses a decoy capable of binding to NF-κB, a transcription factor involved in inflammation, and to E2F, a transcription factor involved in cell proliferation, and describes that the decoy simultaneously inhibits inflammatory response and cell proliferation in an anastomotic site of an artificial blood vessel to prevent restenosis of the artificial blood vessel. In the invention described in Patent Document 2, two transcription factor-binding sites are arranged in tandem on the same strand with an interval of several bases, so that the size thereof is larger than the sum of the size of each binding site and the decoy from the example is 28 mer ("mer" indicates the number of nucleotides in a single strand constituting a double strand; the same shall apply hereinafter). Likewise, Patent Document 3 also describes a double-stranded oligonucleotide decoy having two transcription factor-binding sites, wherein the two transcription factor binding sites are arranged in tandem in the same strand as in Patent Document 2 and may partly overlap and wherein the decoy size is preferably 20 to 40 mer.

PRIOR ART REFERENCES

Patent Documents

Patent Document 1: JP 2010-090103 A
Patent Document 2: WO 2006/043722 A
Patent Document 3: JP 2010-526541 A

SUMMARY OF THE INVENTION

Problems to be Solved by the Invention

Double-stranded oligonucleotides decoys are produced by chemically synthesizing an oligonucleotide having the desired base sequence. Oligonucleic acids are chemically synthesized by condensation synthesis of nucleoside units, and the yield is about 98% per unit in the case of phosphorothioate DNA. Thus, the synthetic yield varies depending on the multiplier of the chain length. For example, in the case of 20 mer, the theoretical synthetic yield is 68%, but in the case of 60 mer, the synthesis yield decreases to 30% and impurities also increase, so that the difference in yield further increases after separation and purification. Therefore, shortening the chain length is an extremely important factor for reducing the synthesis cost. Especially when the size of the oligonucleotide exceeds 15 mer, the synthesis cost greatly increases. When decoys are used as medicines, higher manufacturing costs naturally increase the price of medicines, increase the burden on patients, and become obstacles to widespread use. Therefore, a decoy having a small size is desired.

Thus, an object of the present invention is to provide a double-stranded oligonucleotide decoy comprising two transcription factor-binding sites while keeping its size small.

Means for Solving the Problems

In an attempt to allow a single decoy to contain two transcription-factor binding sites, it has been considered difficult to provide a decoy with a small size such as 15 mer or less since each binding site is about 10 mer. As a result of intensive studies, the present inventors have found that the size of the decoy comprising each binding site for two transcription factors can be greatly reduced by placing each sense strand of each binding site in a different strand and arranging them so that each of the sense strands of each binding site at least partly hybridizes each other, thereby completing the present invention.

That is, the present invention provides a double-stranded oligonucleotide decoy showing binding affinities for two transcription factors, comprising a first binding site for a first transcription factor and a second binding site for a second transcription factor, wherein a first strand comprising the sense strand of the first binding site and a second strand comprising the sense strand of the second binding site are hybridized to form a double strand in which the sense strand of the first binding site and the sense strand of the second binding site are at least partly hybridized.

Effects of the Invention

The present invention first provided a double-stranded oligonucleotide decoy comprising two transcription factor-binding sites while keeping its size small. Since the decoy of the present invention is small in size, and so it is easily and inexpensively synthesized and further, when used as a pharmaceutical agent, can reduce the medicine price, the present invention is expected to greatly contribute to medical treatment using decoy.

MODE FOR CARRYING OUT THE INVENTION

Figure 1:
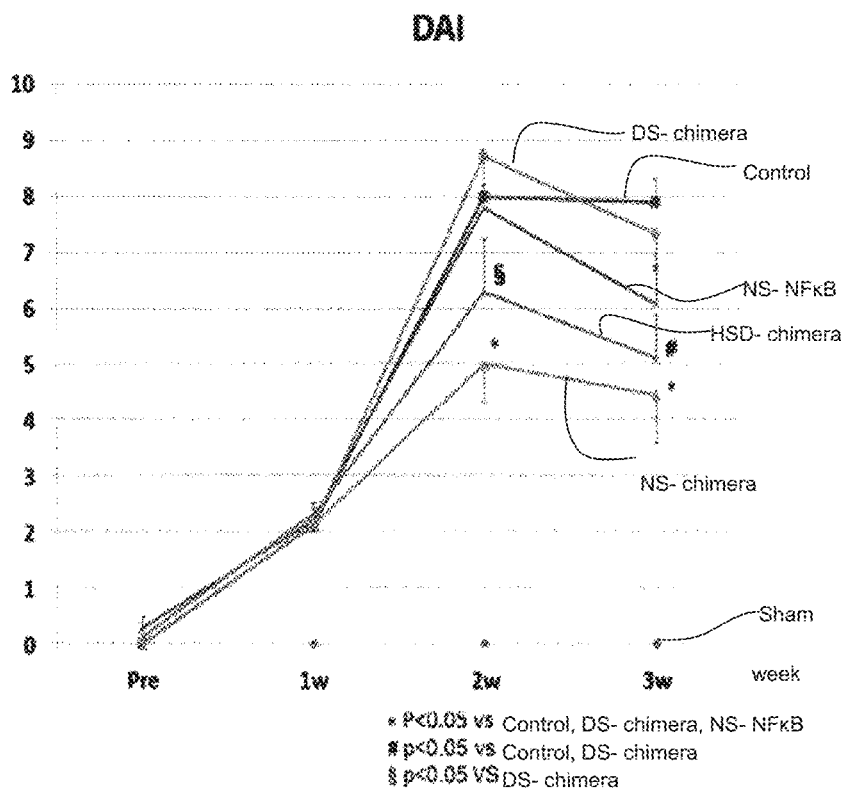
FIG. 1 shows the measurement results of the disease activity index (DAI) in animal experiments using a mouse model of inflammatory bowel disease (IBD) performed in the Examples below.

As described above, the double-stranded oligonucleotide decoy of the present invention comprises a first binding site for a first transcription factor and a second binding site for a second transcription factor. A first strand comprising the sense strand of the first binding site and a second strand comprising the sense strand of the second binding site are hybridized to form a double strand. Further, the sense strand of the first binding site and the sense strand of the second binding site are at least partly hybridized. This structure will now be described by taking as an example NF-κB/STAT6-15mer-B which is a double-stranded oligonucleotide decoy specifically produced in the examples below. Note that 5' end of base sequence is written on the left side unless otherwise specified herein.

The structure of NF-κB/STAT6-15mer-B is represented by the following Formula [I] (SEQ ID NO: 1 and SEQ ID NO: 16)).

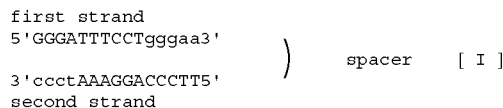

For the NF-κB/STAT6-15mer-B having the structure represented by the Formula [I], the first transcription factor is NF-κB, and the second transcription factor is STAT6. The first and second strands are complementary, and thus the second strand is a complementary strand of the first strand. In the first strand, the sequence GGGATTTCCT (SEQ ID NO: 2), which is designated by capital letters, is the binding site for NF-κB, and in the second strand, the sequence TTCCCAGGAAA (SEQ ID NO: 3), which is designated by capital letters (this sequence is written, in the Formula [I], with its 3' end on the left since it is a complementary strand; and thus this sequence and the sequence represented in the Formula [I] are the same in fact though they are written in opposite directions), is the binding site for STAT6. Consensus sequences of transcription factors are often represented by general formulae. The consensus sequence of NF-κB is GGGRHTYYHC (SEQ ID NO: 4) (wherein R represents A or G, Y represents C or T, and H represents A, C or T), and the consensus sequence of STAT6 is TTCNNNNGAA (SEQ ID NO: 5) (wherein N represents A, G, T or C). Therefore, the binding site GGGATTTCCT (SEQ ID NO: 2) for NF-κB in the first strand is the same as the consensus sequence of NF-κB, except that only one base at the 3' end mismatches with the consensus sequence of NF-κB. The binding site TTCCCAGGAAA (SEQ ID NO: 3) for STAT6 in the second strand contains the whole of the consensus sequence of STAT6. When describing a base sequence, the base sequence of the sense strand is described, though the binding site for and the consensus sequence of the transcription factor are double-stranded. Thus, the base sequences of the binding sites and the consensus sequences as described above are all the base sequences of the sense strands. Thus, the first strand contains the sense strand of the binding site for NF-κB, and the second strand contains the sense strand of the binding site for STAT6. As is apparent from the formula [I], the sequence ATTTCCT in the sense strand of the binding site for NF-κB and the sequence AGGAAA in the sense strand of the binding site for STAT 6 are hybridized, that is, the sense strand of the first binding site and the sense strand of the second binding site are at least partly hybridized.

Thus, in the chimeric decoy of the present invention, the sense strands of two transcription-factor binding sites are placed in different strands and are at least partly hybridized, so that the binding sites for both transcription factors are present at least partly overlapping. This makes it possible to greatly reduce the size of a decoy as compared with the case where two transcription-factor binding sites are arranged in the same strand as described in Patent Documents 2 and 3. Although the size of the chimeric decoy of the present invention is not particularly limited, since the synthesis cost is greatly increased when the size is 16 mer or more, the size is preferably 15 mer or less, whereas since the stability of the double strand is lowered when the strand is too short, the size is preferably 13 mer or more. Considering binding activity and in vivo stability comprehensively, the most preferred size is 15 mer.

The transcription-factor binding sites each preferably contains the whole of the consensus sequence of each transcription factor from the viewpoint of binding activity, but in that case, the freedom of selection in the combination of transcription factors is greatly limited. On the other hand, as described in detail in the examples below, since the above-described NF-κB/STAT6-15mer-B shows excellent transcription factor inhibitory activity, the binding site for each transcription factor may have one single base substitution compared with the consensus sequence of each transcription factor (as described above, in NF-κB/STAT6-15mer-B, the binding site for NF-κB in the first strand has one single base substitution compared with the consensus sequence of NF-κB). This single base substitution greatly increases the degree of freedom for selecting combination of transcription factors and makes it possible to employ various combinations of transcription factors. Although up to two base substitutions can be tolerated, one single base substitution is preferred from the viewpoint of binding activity.

For the two transcription factors, any combination can be used as long as the sense strands of the binding sites for them can be at least partly hybridized. In addition to the above-described combination of NF-κB and STAT6, decoys were prepared in the Examples below using the combinations of, for example, NFκKB and Ets1, NFκKB and NF-AT, NF-κB and STAT1, and NFκKB and NF-IL6. Even if the combination of transcription factors is the same, two or more decoys differing in base sequence can often be prepared. In the Examples below, decoy having the structure represented by the following Formula [II] (NF-κB/STAT6-15mer-A) (SEQ ID NO: 6 and SEQ ID NO: 17) was also prepared as a combination of NF-κB and STAT6.

```
first strand
5'GGGACTTCCCatgaa3'    )
                       )   spacer    [ II ]
3'ccctGAAGGGTACTT5'    )
second strand
```

Since the consensus sequence of Ets1 is MGGAW (wherein M is A or C, and W is A or T), decoys having the structures represented by the following Formulae [III] and [IV] (NF-κB/Ets1-15mer-A (SEQ ID NO: 7 and SEQ ID NO: 18) and NF-κB/Ets1-15mer-B (SEQ ID NO: 8 and SEQ ID NO: 19)) were prepared as combinations of NF-κB and Ets1.

```
first strand
5'gGGGACTTCCTGctc3'    )
                       )   spacer    [ III ]
3'ccccTGAAGGACgag5'    )
second strand first strand
5'gGGGACTTCCGGgtg3'    )
                       )   spacer    [ IV ]
3'ccccTGAAGGCCcac5'    )
second strand
```

Since the consensus sequence of NF-AT is WGGAAANHN (wherein W is A or T, N is A, G, T or C, and H is A, T or C), decoys having the structures represented by the following Formulae [V] and [VI] (NF-κB/NF-AT-15mer-A (SEQ ID NO: 9 and SEQ ID NO: 20) and NF-κB/NF-AT-15mer-B (SEQ ID NO: 10 and SEQ ID NO: 21)) were prepared as combinations of NF-κB and NF-AT.

```
first strand
5'gGGGAATTTTCCtct3'    )
                       )   spacer    [ V ]
3'ccccTTAAAAGGAga5'    )
second strand first strand
5'gGGGGATTTTCCtct3'    )
                       )   spacer    [ VI ]
3'ccccCTAAAAGGAga5'    )
second strand
```

Since the consensus sequence of STAT1 is TTCNNN-GAA (wherein N is A, G, T or C), decoys having the structures represented by the following Formulae [VII] and [VIII] (NF-κB/STAT1-15mer-A (SEQ ID NO: 11 and SEQ ID NO: 22) and NF-κB/STAT1-15mer-B (SEQ ID NO: 12 and SEQ ID NO: 23)) were prepared as combinations of NF-κB and STAT1.

```
first strand
5'GGGACTTCCAggaat3'    )
                       )   spacer    [ VII ]
3'ccctgAAGGTCCTTa5'    )
second strand first strand
5'GGGACTICCCggaat3'    )
                       )   spacer    [ VIII ]
3'ccctgAAGGGCCTTa5'    )
second strand
```

Since the consensus sequence of NF-IL6 is TKNNG-NAAK (wherein K is G or T, and N is A, G, T or C), decoys having the structures represented by the following Formulae [IX] and [X] (NF-κB/NF-IL6-15mer-A (SEQ ID NO: 13 and SEQ ID NO: 24) and NF-κB/NF-IL6-15mer-B (SEQ ID NO: 14 and SEQ ID NO: 25)) were prepared as combinations of NF-κB and NF-IL6.

```
first strand
5'GGGATTTCCCaatct3'    )
                       )   spacer    [ IX ]
3'cccTAAAGGGTTaga5'    )
second strand first strand
5'GGGATTCCGcaatct3'    )
                       )   spacer    [ X ]
3'cccTAAGGCGTTaga5'    )
second strand
```

Combinations of transcription factors are not limited to the above examples, and other examples include, but are not limited to, a combination of Est-1 and STAT-1, a combination of Est-1 and STAT-6, a combination of Est-1 and NF-AT, a combination of Est-1 and NF-IF6, a combination of STAT-1 and NF-IL6, and a combination of STAT-6 and NF-IL-6. Since the consensus sequence of each transcription factor is well known, one skilled in the art can easily design the chimeric decoy of the present invention for a combination of two selected transcription factors. However, since the above-mentioned requirement need to be satisfied, it is not always possible to design the chimeric decoy of the present invention for any and all combinations of transcription factors.

The oligonucleotide constituting the chimeric decoy of the present invention may be DNA or RNA, but DNA is preferred from the viewpoint of the binding activities to transcription factors and the stability.

The chimeric decoy of the present invention may be a simple double strand, or may be a hairpin or dumbbell (staple) decoy in which one or both ends of each strand are bound via a spacer. Hairpin and dumbbell decoys are preferred because of their higher stability. When comprehensively evaluating the binding activities to transcription factors and the stability, the hairpin decoy is most preferred.

The hairpin decoy has a structure in which the 3' end of the first strand and the 5' end of the second strand are bound via a spacer, as shown in the above-described Formulae [I] to [X]. Hairpin double-stranded oligonucleotide decoys themselves are well known and are described in detail in, for example, Patent Document 1. Examples of the spacer include $-OPO_2-(OCH_2CH_2)n_3-OPO_2O-$, $-OPO_2-(OCH_2CH_2CH_2)n_3-OPO_2O-$ and $-OPO_2O-(CH_2)n_4-OPO_2O-$, preferably $-OPO_2-(OCH_2CH_2)n_3-OPO_2O-$ and $-OPO_2O-(CH_2)n_4-OPO_2O-$. Here, $n_3$ represents an integer of 4 to 8, preferably an integer of 5 to 7, more preferably 6, and $n_4$ represents an integer of 3 to 12. The $-OPO_2O-$ at each end of the spacer each represents a phosphodiester bond bound to the 3' or 5' position of the sugar of the adjacent nucleotide. The portion excluding $-OPO_2O-$ at both ends of the spacer may be referred to as "spacer moiety" below. The spacer moieties of the double-stranded oligonucleotide decoys having the structure represented by the formulae [I] to [X] prepared in the examples below are all dodecylene groups.

The hairpin double-stranded oligonucleotide decoy can be synthesized, for example, by first synthesizing a single-stranded oligonucleotide to which a spacer is to be bound at its 5' end by a conventional method; attaching a spacer to its 5' end; attaching the 3' position of a prescribed nucleotide to the other end of the spacer; and further attaching prescribed oligonucleotides to the 5' end of the nucleotide one by one by a conventional method. Reagents for introducing various spacers (derivatives of spacers) for preparing hairpin double-stranded oligonucleotides are commercially available, and hairpin double stranded oligonucleotides can be easily prepared by using these commercially available spacer reagents according to their instructions. Examples of the commercially available reagents that can be used include the following.

1. Reagents for Introducing a Spacer Moiety Comprising Repeating Ethylene Glycol Units:
(1) 18-O-Dimethoxytritylhexaethyleneglycol,1-[(2-cyanoethyl)-(N,N-diisopropyl)]-phosphoramidite
(trade name: Spacer Phosphoramidite 18, Glen Research, USA)
(binding a spacer moiety composed of 6 ethylene glycol units)
(2) 9-O-Dimethoxytrityl-triethylene glycol,1-[(2-cyanoethyl)-(N,N-diisopropyl)]-phosphoramidite
(trade name: Spacer Phosphoramidite 9, Glen Research, USA)
(binding a spacer moiety composed of 3 ethylene glycol units)
(3) DMT-dodecane-Diol phosphoramidite
(trade name: Spacer 12, ChemGenes, USA)
(binding a spacer moiety composed of 4 ethylene glycol units)

2. Reagents for introducing a spacer moiety comprising alkylene chain:
(1) 3-(4,4'-Dimethoxytrityloxy)propyl-1-[(2-cyanoethyl)-(N,N-diisopropyl)]-phosphoramidite
(trade name: Spacer Phosphoramidite C3, Glen Research, USA)
(binding a spacer moiety composed of propylene chain)
(2) DMT-butane-Diol phosphoramidite
(trade name: C-4 Spacer, ChemGenes, USA)
(binding a spacer moiety composed of butylene chain)
(3) DMT-hexane-Diol phosphoramidite
(trade name: C-6 Spacer, ChemGenes, USA)
(binding a spacer moiety composed of hexylene chain)
(4) DMT-nonane-Diol phosphoramidite
(trade name: C-9 Spacer, ChemGenes, USA)
(binding a spacer moiety composed of nonylene chain)
(5) 12-(4,4'-Dimethoxytrityloxy)dodecyl-1-[(2-cyanoethyl)-(N,N-diisopropyl)]-phosphoramidite
(trade name: Spacer C12 CE Phosphoramidite, Glen Research, USA)
(binding a spacer moiety composed of dodecylene chain)

In the oligonucleotide according to the present invention, in order to impart appropriate biochemical stability, all or a part of internucleotide linkages may be subjected to a modification for nuclease resistance such as phosphorothioation. In other words, in the chimeric decoy of the present invention, the oligonucleotide part is preferably DNA in essence, but bonds between at least two adjacent nucleotides (and/or, in the case of a nucleotide adjacent to a spacer moiety, a bond between the nucleotide and the spacer moiety) may be subjected to a modification for nuclease resistance to increase the resistance to nuclease. The term "modification for nuclease resistance" as used herein means a modification that makes DNA less susceptible to degradation by nuclease than natural DNA, and such DNA modification itself is well-known. Examples of the modification for nuclease resistance include phosphorothioation (sometimes referred to herein as "sulfur modification"), phosphorodithioation, and phosphoroamidation. Among them, sulfur modification is preferred. Sulfur modification means converting one of two non-bridging oxygen atoms bound to a phosphorus atom that constitutes a phosphodiester bond between adjacent nucleotides to a sulfur atom as described above. Techniques for sulfur modification of any linkages between adjacent nucleotides themselves are well known. For example, it can be easily carried out using a sulfur modification reagent (CPRII, 3H-1,2-benzodithiole-3-one-1,1-dioxide) (Glen Research). Also, sulfur-modified oligonucleotides are commercially synthesized. In the present description and the claims, a base sequence includes those in which a part or all of the linkages between the nucleotides and between the spacer and the nucleotide is sulfur-modified or not sulfur-modified at all, unless the context clearly indicates otherwise.

The chimeric decoy of the present invention can be administered as it is, or can also be administered after it is conjugated with a substance constituting an appropriate drug delivery system (DDS). Examples of DDSs for an oligonucleotide include liposomes containing cationic substances, cell membrane permeable peptides, polymers containing them, and atelocollagen. These can also be used in administration of the chimeric decoys of the present invention. Besides these, the chimeric decoy of the present invention can also be conjugated to PLGA (polylactic acid/glycolic acid copolymer) nanoparticles for administration.

PLGA nanoparticles are particles having a diameter of tens of nanometers to hundreds of nanometers composed of PLGA. PLGA nanoparticles are manufactured as particles for DDS (e.g., Hosokawa Micron), so commercially available technology can be preferably used. When the chimeric decoy of the present invention is conjugated to PLGA nanoparticles, the 5' end of the first strand of the chimeric decoy is preferably conjugated to PLGA nanoparticles via a disulfide linker and an amino linker. This can be carried out, for example, by reacting a PLGA-NHS ester with the chimeric decoy to obtain a PLGA-conjugated chimeric decoy and further making it into a nano-sized particle by utilizing the Marangoni effect, and detailed preparation methods are also described in the Examples below. It is not known to bind PLGA nanoparticles to decoys for the DDS of double-stranded oligonucleotide decoys.

Since the chimeric decoy of the present invention has binding sites for two transcription factors, it can reduce the activities of these two transcription factors (it should be noted, however, that two transcription factors are not simultaneously bound to a single decoy molecule). Therefore, the chimeric decoy of the present invention can be used for treatment and prevention of various diseases caused by high activities of these two transcription factors. Thus, decoys having a binding site for NF-κB can be used as an active ingredient in pharmaceutical agents in which an NF-κB decoy is used as an active ingredient. Such pharmaceutical agents are recognized to be effective for the treatment and prevention of various diseases described below:

Vascular restenosis, acute coronary syndrome, cerebral ischemia, myocardial infarction, reperfusion injury associated with ischemic disease, atopic dermatitis, psoriasis vulgaris, contact dermatitis, keloid, decubitus, ulcerative colitis, Crohn's disease, nephropathy, glomerulosclerosis, albuminuria, nephritis, renal failure, chronic rheumatoid arthritis, osteoarthritis, intervertebral disc degeneration, asthma, chronic obstructive pulmonary disease, cystic fibrosis, aortic aneurysm, cerebral aneurysm;

as well as
1. Immune system diseases, including
    Aortitis syndrome (Takayasu's arteritis)
    Buerger's disease (Buerger's disease)
    Polyarteritis nodosa
    Wegener's granulomatosis
    Allergic granulomatous angiitis (Churg-Strauss syndrome)
    Systemic lupus erythematosus
    Polymyositis/dermatomyositis complex
    Sjogren's syndrome
    Adult-onset Still's disease;
2. Neuromuscular diseases, including
    Parkinson's disease
    Amyotrophic lateral sclerosis (ALS)
    Multiple sclerosis (MS);
3. Respiratory diseases, including
    Idiopathic interstitial pneumonia
    Sarcoidosis
    Primary pulmonary hypertension;
4. Digestive system diseases, including
    Autoimmune hepatitis
    Fulminant hepatitis
    Severe acute pancreatitis;
5. Skin and connective tissue diseases, including
    Scleroderma;
6. Bone and joint diseases, including
    Diffuse spinal canal stenosis; and
7. Kidney and urinary system diseases, including
    IgA nephropathy
    Rapidly progressive glomerulonephritis.

Similarly, a decoy having a binding site for STAT6 is useful for treating and preventing, for example, respiratory diseases such as asthma, allergic diseases such as allergic rhinitis and allergic conjunctivitis, atopic asthma, atopic dermatitis, ulcerative colitis, Crohn's disease, arthropathy, chronic pain, and cancer; a decoy having a binding site for Ets1 is useful for treating and preventing, for example, ischemic heart failure, ischemic cerebrovascular disease, ischemic lung disease, worse prognosis after organ transplantation or organ surgery, reperfusion injury, post-PTCA restenosis, nephritis, hepatitis, arthritis, acute renal failure, chronic renal failure, arteriosclerosis, rheumatism, multiple sclerosis, and cancer; a decoy having a binding site for NF-AT is useful for treating and preventing, for example, osteoporosis/arthropathy, autoimmune disease, infectious disease, and cancer; a decoy having a binding site for STAT1 is useful for treating and preventing, for example, respiratory diseases such as chronic obstructive pulmonary disease, cystic fibrosis, asthma, eosinophilic cough, bronchitis, sarcoidosis, pulmonary fibrosis, rhinitis, and sinusitis; and a decoy having a binding site for NF-IL6 is useful for treating and preventing, for example, immune cell proliferative disease, psoriasis, pemphigus vulgaris, Behcet's syndrome, acute respiratory distress syndrome, ischemic heart disease, post-dialysis syndrome, leukemia, rheumatoid arthritis, acquired immunodeficiency syndrome, angiitis, lipid histiocytosis, and sepsis.

Since administration of the chimeric decoy of the present invention can simultaneously reduce the activities of two transcription factors, the chimeric decoy of the present invention may be used for reducing the activities of two transcription factors that are desired to be simultaneously reduced in activity. For example, two transcription factors effective for treating or preventing the same disease can be combined to further enhance the therapeutic or preventive effect, or two functionally-related transcription factors may be combined. For the treatment or prevention of a wide range of diseases, completely unrelated transcription factors may also be combined.

When the chimeric decoy of the present invention is used for medicinal uses, the route of administration of the decoy is not particularly limited, but may be preferably parenteral administration such as intravenous administration, intramuscular administration, subcutaneous administration, dermal administration, or direct administration to the target organ or tissue. The dosage is appropriately selected depending on, for example, the target disease, symptoms of the patient, and the route of administration, but usually 0.1 to 10000 nmol, preferably 1 to 1000 nmol, and more preferably 10 to 100 nmol per day for an adult may be administered. Formulation can be carried out by a conventional method. For example, in the case of an injection solution, it can be in the form of a solution in which the chimeric decoy of the present invention is dissolved in physiological saline. Additives commonly used in the field of pharmaceutical preparations such as preservatives, buffers, solubilizers, emulsifiers, diluents, and isotonizing agents may be appropriately mixed during formulation. In addition, the formulation may contain other medicinal ingredients.

The present invention will now be described in detail with reference to Examples. However, the present invention is not limited to the following Examples. For all hairpin decoys in the following examples, their spacer moieties are dodecylene group. Further, in all the Examples, all the internucleotide linkages are phosphorothioated.

EXAMPLES 1-10

1. Preparation of Double-Stranded Oligonucleotide Decoy

NF-κB/Ets1-15mer-A (SEQ ID NO: 7, Formula [III]) (Example 1), NF-κB/Ets1-15mer-B (SEQ ID NO: 8, Formula [IV]) (Example 2), NF-κB/NF-AT-15mer-A (SEQ ID NO: 9, Formula [V]) (Example 3), NF-κB/NF-AT-15mer-B (SEQ ID NO: 10, Formula [VI]) (Example 4), NF-κB/STAT1-15mer-A (SEQ ID NO: 11, Formula [VII]) (Example 5), NF-κB/STAT1-15mer-B (SEQ ID NO: 12, Formula [VIII]) (Example 6), NF-κB/STAT6-15mer-A (SEQ ID NO: 6, Formula [II]) (Example 7), NF-κB/STAT6-15mer-B (SEQ ID NO: 1, Formula [I]) (Example 8), NF-κB/NF-IL6-15mer-A (SEQ ID NO: 13, Formula [IX]) (Example 9) and NF-κB/NF-IL6-15mer-B (SEQ ID NO: 14, Formula [X]) described above were prepared. The hairpin decoys were each synthesized by chemically synthesizing a second strand; then attaching a spacer (dodecylene chain) to the 5' end thereof, attaching the 3' position of a prescribed nucleotide to the other end of the spacer; and further attaching prescribed oligonucleotides one by one to the 5' end of the nucleotide by a conventional method. Bonding of the dodecylene chain was carried out using a commercially available reagent (trade name: Spacer C 12 CE Phosphoramidite, Glen Research, USA) according to its instructions.

2. Binding Activity Assay

For each of the double-stranded oligonucleotide decoys prepared in 1, the binding activity was measured. The binding activity was measured in the following manner.

(1) Binding Activity Assay

Test Method

Using a commercially available transcription factor assay kit (TransAM™ NF-κB p65: Cat. No. 40096: TransAM™ STAT Family: Cat. No. 42296, TransAM™ NFATc1: Cat. No. 40296, TransAM™ C/EBP α/β: Cat. No. 44196, Active Motif, Inc), the decoy solution and a Jurkat cell (derived from human T-cell lymphoma) or HeLa cell (derived from human cervical cancer) nuclear extract were added to a plate on which a consensus sequence of each transcription factor was immobilized, and then allowed to react at room temperature for 1 hour. After washing, a primary antibody (anti-NF-κB p65 antibody) and a secondary antibody (HRP-anti-IgG antibody) were added according to the kit instructions. After washing, the measurement was carried out by colorimetric method.

Evaluation Method

The concentration value of each of the decoy solutions was converted into logarithm, and an approximate curve was prepared by plotting the concentration values converted into logarithm (5 to 10 points within a concentration range of 0.005 to 400 nmol/L) on the horizontal axis and the percentage value of each of the groups on the vertical axis to calculate the IC50 (inhibition concentration 50%) at each reaction time.

(2) Confirmation of Binding by Gel Shift Assay

Test Method

Confirmation of binding to STAT 6 and Est-1 by gel shift assay was carried out using a commercially available assay kit (Light Shift™ Chemiluminescent EMSA kit: Cat. No. p74026, Takara Bio), by charging a test tube with binding sequences for STAT6 and Est-1 as biotinylated probe sequences and with the decoy solution and a HeLa cell (derived from human cervical cancer) nuclear extract, and then allowing the mixture to react at room temperature for 30 minutes with reagents attached to the kit. The resulting reaction solution was subjected to polyacrylamide gel electrophoresis, transferred to a nylon membrane, cross-linked with UV, blocked, and then added with Stabilized Streptavidin-Horseradish Peroxidase Conjugate according to the kit instructions, washed, and subjected to chemiluminescence.

Evaluation Method

Among the concentration values (1, 10, 100 pmol) of each added decoy solution, the concentration at which the band of STAT 6 or Est-1 completely disappeared was regarded as the effective concentration.

The results are shown in Table 1 below.

TABLE 1

Binding activities to transcription factors

| | | Evaluation of binding activity by ELISA method: $IC_{50}$ (nM) | | | | Confirmation of binding by EMSA method | |
|---|---|---|---|---|---|---|---|
| | Sequence name | NF-κB | STAT1 | NF-AT | NF-IL6 | ETS-1 | STAT6 |
| 7 | NF-kB/Ets1-15mer-A | 5.51 | — | — | — | 100 pmol* | — |
| 8 | NF-kB/Ets1-15mer-B | 6.09 | — | — | — | 100 pmol* | — |
| 9 | NF-kB/NF-AT-15mer-A | 5.69 | — | 132.52 | — | — | — |
| 10 | NF-kB/NF-AT-15mer-B | 1.67 | — | 146.11 | — | — | — |
| 11 | NF-kB/STAT1-15mer-A | 31.78 | 13.87 | — | — | — | — |
| 12 | NF-kB/STAT1-15mer-B | 9.94 | 19.14 | — | — | — | — |
| 13 | NF-kB/STAT6-15mer-A | 18.83 | — | — | — | — | 10 pmol* |
| 14 | NF-kB/STAT6-15mer-B | 3.61 | — | — | — | 100 pmol* | 10 pmol* |
| 15 | NF-kB/NF-IL6-15mer-A | 2.28 | — | — | >400 | — | — |
| 16 | NF-kB/NF-IL6-15mer-B | 9.51 | — | — | 164.59 | — | — |

—: Not tested
*Amount of decoy at which the band in EMSA disappeared

As shown in Table 1, it was confirmed that the chimeric decoys of the present invention bound to two transcription factors that bind to the two binding sites contained in each decoy.

3. Effect on Cytokine Production

Test Method

Mouse macrophage-derived RAW 264.7 cells were seeded (in a 24-well plate: at $4.0 \times 10^4$ cells/well/250 µL) and cultured at 37° C. and 5% $CO_2$ for 24 hours (in RPMI 1640 containing 10% FBS). Using a gene transfer reagent (Fu-GENE HD Transfection Reagent: Cat. No. E 2311, Promega), 20 nmol/L of each of the decoy solutions was transfected into the cells. Then, the cells were stimulated with LPS (at 100 ng/mL, for 24 hours). The culture supernatant was collected, and the concentration of each cytokine was measured using a commercially available cytokine ELISA kit (Mouse IL-1 beta/IL-1F2 Quantikine ELISA Kit: Cat. No. MLB00C, Mouse IL-6 Quantikine ELISA Kit: Cat. No. M6000B, Mouse TNF-alpha Quantikine ELISA Kit: Cat. No. MTAOOB, R&D systems).

Evaluation Method

The cytokine inhibition rate (%) of each decoy sequence was calculated by the following equation:

Cytokine inhibition rate (%)=100−(cytokine concentration in a decoy-added group/cytokine concentration in a control group(LPS stimulation alone))×100

The results are shown in Table 2 below.

TABLE 2

| Group | IL-1β | IL-6 | TNF-α |
|---|---|---|---|
| NF-κB/Ets1-15mer-A | 41.7 | 43.5 | 33.4 |
| NF-κB/Ets1-15mer-B | 58.5 | 46.8 | 41.6 |
| NF-κB/NF-AT-15mer-A | 46.9 | 54.0 | 38.8 |
| NF-κB/NF-AT-15mer-B | 39.8 | 51.7 | 24.4 |
| NF-κB/STAT1-15mer-A | 26.5 | 73.0 | 54.7 |
| NF-κB/STAT1-15mer-B | 33.5 | 63.3 | 43.4 |
| NF-κB/STAT6-15mer-A | 8.9 | 64.5 | 52.1 |
| NF-κB/STAT6-15mer-B | 41.4 | 82.2 | 53.5 |
| NF-κB/NF-IL6-15mer-A | 39.7 | 83.5 | 47.9 |
| NF-κB/NF-IL6-15mer-B | 42.6 | 69.6 | 44.0 |

As shown in Table 2, it was confirmed that the chimeric decoys of the present invention inhibited the productions of the three cytokines investigated. From the results shown in Table 2, Example 8 (NF-κB/STAT6-15mer-B) is considered to exert the most excellent effect from a comprehensive viewpoint. Thus, in the following examples, NF-κB/STAT6-15mer-B was used.

EXAMPLE 11

Binding to PLGA Nanoparticles

NF-κB/STAT6-15mer-B prepared in Example 8 above was bound to PLGA nanoparticles. Specifically, this operation was carried out as follows. When the hairpin oligonucleotide was synthesized, an amino linker was added to the 5' end. On the other hand, the carboxyl group at the terminal of PLGA (manufactured by Wako Pure Chemical Industries) was converted to highly-reactive N-hydroxysuccinimide (NHS) ester, and this was coupled with the amino group at the terminal of the oligonucleotide by an amide bond to form a PLGA-conjugated oligonucleotide. Further, in order to promptly release the oligonucleotide in a cell in the reduced state, a disulfide bond was inserted between the oligonucleotide and the amino group, which disulfide bond was also added on the synthesizer. A commercially available product for oligonucleotide synthesis can be used for the amino linker or the disulfide bond-containing linker. The resulting PLGA-conjugated NF-κB/STAT6-15mer-B was mixed with PLGA, acetone, ethanol and water and dropped into a mixed solvent of polyvinyl alcohol, chitosan and water to form particles. Then, the solvent was distilled away and filtered under pressure to obtain a solution containing particles. In addition, freeze-drying was carried out when necessary.

EXAMPLE 12

Animal Study 1

1. Mouse Model of IBD (Inflammatory Bowel Disease)

Implementation Method (1) Animal Model

A chronic phase model was used in which C57BL/6J mice (male, 6 week-old) were allowed to freely drink 1.5% DSS (dextran sodium sulfate) solution for 21 days and treatment was started on Day 7 when the pathology was established.

(2) Group Composition

The administrated group and dosage are shown in Table 3 below. For the administration method, 200 µL/mouse of each substance to be administered was administered by gavage (equivalent to 10 mL/kg when the mouse weight was 20 g). The administration was performed six times in total, three days a week from Day 7 (Days 7, 9, 11, 14, 16 and 18) with the drinking start date set as Day 0.

TABLE 3

| Study group | Substance with drinking water | Substance to be administered | Dosage (mg/kg) | Frequency of administration | Number of animals |
|---|---|---|---|---|---|
| Sham | Water | — | — | — | 4 |
| Control | 1.5% DSS | water (vehicle) | 0 | 3 times a week | 15 |
| NS-chimera | 1.5% DSS | NF-κB/STAT6-HSD-PLGA-NS | 10 (50) | 3 times a week | 15 |
| NS-NFκB | 1.5% DSS | NFκB-HSD-PLGA-NS | 10 (50) | 3 times a week | 15 |
| HSD-chimera | 1.5% DSS | NFκB/STAT6-HSD | 10 | 3 times a week | 15 |

Substance to be administered: NF-κB/STAT6-HSD-PLGA-NS = a HSD-PLGA-nanoparticle of NF-κB/STAT6-15mer-B (HSD means hairpin type), NF-κB-HSD-PLGA-NS = a HSD-PLGA-nanoparticle of HSD 13 mer PS (C12), NFκB/STAT6-HSD = NF-κB/STAT6-15mer-B
Dosage: dosage as HSD (dose in parentheses as particle)
HSD 13 mer PS (C12) is a double-stranded oligonucleotide having the base sequence of SEQ ID NO: 15 which has been changed to hairpin type with a spacer in which the spacer moiety is dodecylene group.

(3) Evaluation

For drug evaluation, body weights at the start of drinking (Day 0), Day 7, Day 14 and at dissection (Day 21) were measured and DAIs (Disease Activity Index) was evaluated. The colon length was measured at dissection.

3) Test Results

Figure 2:
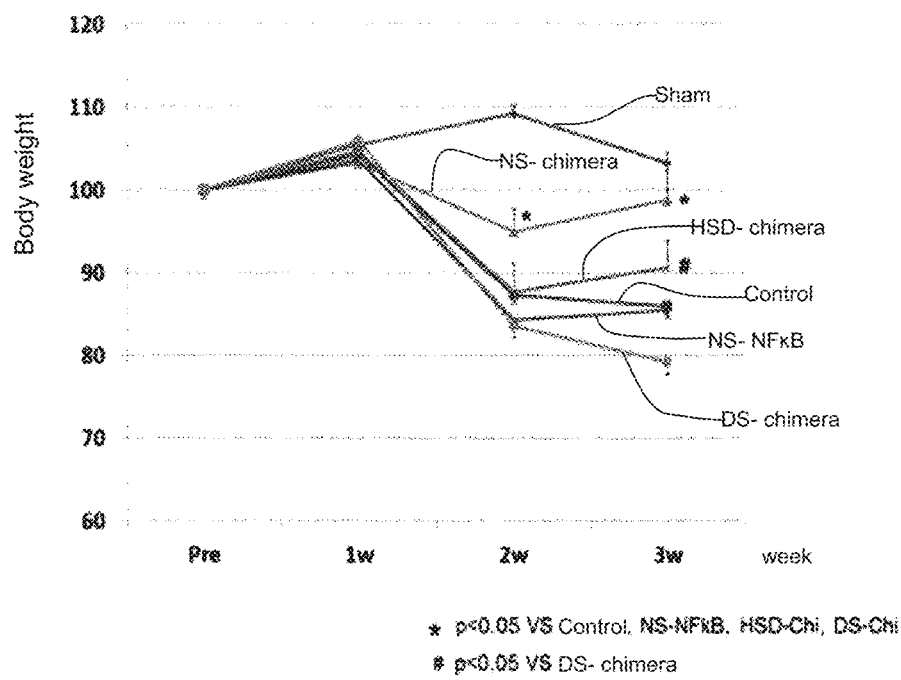
FIG. 2 shows the time-dependent changes of bodyweights in animal experiments using a mouse model of inflammatory bowel disease (IBD) performed in the Examples below.
Figure 3:
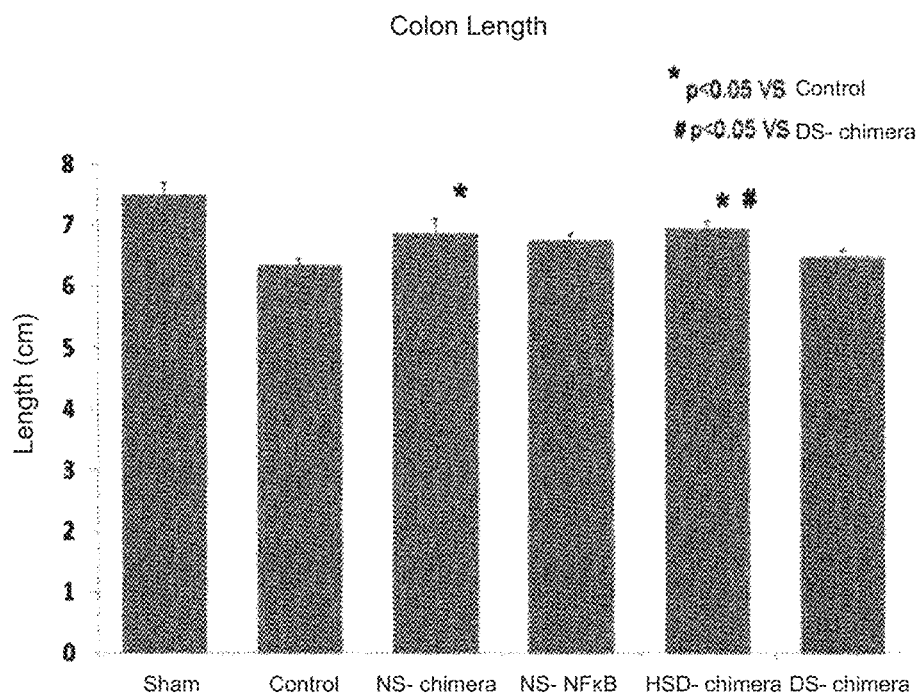
FIG. 3 shows the comparison of the colon lengths in animal experiments using a mouse model of inflammatory bowel disease (IBD) performed in the Examples below.

The results are shown in FIGS. 1 to 3. In the evaluation of DAI, the NS-chimera group showed suppression of symptom progression from the second week and the HSD-chimera group showed a significantly lowered DAI value at the third week. Although the degree of weight loss was similar to that of DAI, the body weights of the NS-chimera, NS-NFκKB and HSD-chimera group at the third week increased from those at the second week. With respect to the colon length, significant suppression of shortening was observed in the NS-chimera and HSD-chimera group.

Compared with the NS-NFκKB group, the HSD-chimera group had a higher effect in any of the evaluation items.

2. Mouse Model of OVA-Induced Asthma

Implementation Method (1) Animal Model

Female C57BL/6J mice (10 to 12 week-old) were intraperitoneally sensitized with 20 μg of OVA (ovalbumin)+2 mg of Alum on the first day (Day 0) and Day 14. Inflammation was induced in the respiratory tract by inhalation of 1% OVA for 20 min on Day 21, 22 and 23 to prepare a pathological condition model.

(2) Group Composition

The administrated group and dosage are shown in Table 4 below. Each substance to be administered was administered intratracheally only once at 20 nmol on Day 18.

TABLE 4

| Study group | Sensitization | Substance to be administered | Dosage (nmol/head) | Frequency of administration | Number of animals |
|---|---|---|---|---|---|
| Sham | − | physiological saline | — | once | 7 |
| Control | + | physiological saline | — | once | 10 |
| Scrambled | + | scrambled decoy (negative control) | 20 | once | 8 |
| NF-κB | + | NF-κB decoy | 20 | once | 10 |
| NF-κB/STAT6 | + | HSD-NFκB/STAT6 | 20 | once | 9 |

(3) Evaluation

For drug evaluation, mice were inhaled with Methacholine, a bronchoconstrictor (3.1, 6.25, 12.5 and 25 mg/mL) on Day 24, and the airway resistance was measured as follows. Methacholine (MCh)-induced airway hyperreactivity (AHR) was measured under anesthesia 24 hours after the last OVA challenge (Day 24). Mice were subjected to tracheostomy under general anesthesia, cannulation and mechanical ventilation (150 breaths/minute, 200 μL tidal volume). Pancuronium bromide (0.1 mg/kg) was administered for inhibiting the neuromuscular reaction. Invasive airway resistance and compliance were then measured by Resistance & Compliance System (Buxco Electronics). After baseline measurement, 10 μL of PBS or MCh (3.125 mg/ml, 6.25 mg/ml, 12.5 mg/ml, and 25 mg/ml) was sprayed into the endotracheal tube over 30 seconds and allowed to react over 270 seconds.

3) Test Results

Figure 4:
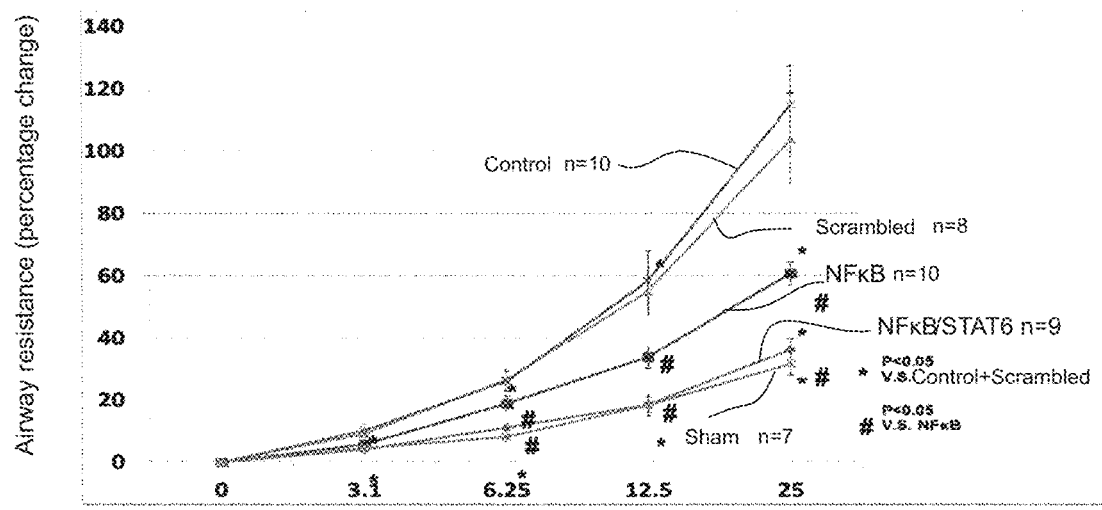
FIG. 4 shows the measurement results of the airway resistance after administering increasing amounts of methacholine in a mouse model of ovalbumin (OVA)-induced asthma which is pre-treated with various decoys, obtained in the Examples below.

The results are shown in FIG. 4. Since AHR is a major feature of asthma and an important therapeutic target, the present inventors investigated the effect of NF-κB decoy ODN and chimeric decoy ODN on MCh-induced dose-dependent AHR enhancement in OVA-treated mice. For mice treated with physiological saline (control group) and scrambled decoy ODN, the airway resistance remarkably increased depending on the dose of MCh, and there was no difference in responses to MCh between the two groups. On the other hand, for mice treated with NF-κB decoy ODN and chimeric decoy ODN, the increase in airway resistance was remarkably inhibited. Response to MCh was completely improved by chimeric decoy ODN, and the effect of chimeric decoy ODN was significantly higher than the effect of NF-κB decoy ODN only (FIG. 4).

3. Further Experiments Using Mouse Model of OVA-Induced Asthma

Method (1) Effects of Inhibition of NF-κB and/or STAT6 on Pulmonary Allergic Reaction In order to evaluate the effects of inhibition of NF-κB and/or STAT6 on pulmonary allergic reaction, chimeric decoy ODN, NF-κB decoy ODN, or scrambled decoy ODN (20 nmol in 25 μL physiological saline per mouse) was intratracheally administered to OVA-sensitized mice on Day 18 (3 days before OVA inhalation) using MicroSprayer® aerosolizer (Model 1A-1C, Penn-Century, Pa.) capable of aerosolizing chemical-containing solutions. For control mice and sham-treated mice, physiological saline (25 μL per mouse) was administered intratracheally. In the administration of decoy ODN, mice were anesthetized by intraperitoneal injection of xylazine (10 mg/Kg) and ketamine (100 mg/Kg).

Intratracheal administration of FITC-labeled chimeric decoy ODN was also carried out in OVA-sensitized mice 3 days before inhalation of OVA, and the lung tissues were obtained 1 day after OVA challenge. Frozen sections (5 μm) of these lung tissues were prepared and examined using fluorescence microscopy.

This experimental protocol was approved by a local animal care and use committee. This study was conducted under the supervision of an animal care and use committee in compliance with the guideline on animal experiments of Osaka University School of Medicine and the Act on Welfare and Management of Animals of Japan (Law No. 105).

(3) Bronchoalveolar Lavage Analysis

Immediately after the AHR measurement, the airway lumen of each mouse was washed three times with 0.4 mL of ice-cold PBS. Total cell number in the BALF was counted using hemocytometer. Cells were stained with Diff-Quik solution to discriminate blood cells. Using ELISA, the concentrations of IL-4 (R&D Systems), IL-5 (Thermo Fisher Scientific) and IL-13 (R&D Systems) in the BALF were also measured.

(4) Electrophoresis Mobility Shift Assay

Nuclear extracts were prepared from the lung tissues by a conventional method. Expressions of NF-κB and STAT6 in the nuclear extracts after OVA challenge were analyzed using a gel shift assay system (Promega, Wis.). As a primer, ODN (5'-CCTTGAAGGGATTTCCCTCC-3' (SEQ ID NO: 26); only the sense strand is shown) comprising an NF-κB binding site or ODN (5'-GTATTTCCCAGAAAAGGAAC-3' (SEQ ID NO: 27); only the sense strand is shown) comprising a STAT6 binding site was labeled with [γ-$^{32}$P] ATP at the 3' end. A conjugated mixture (10 μL) containing $^{32}$P-labeled primer (10,000 cpm) and 1 μg of poly(deoxyinosinic-deoxycytidylic) acid was incubated with 10 μg of the nuclear extract for 30 minutes at room temperature and then applied to a 6% polyacrylamide gel. A sample incubated with an excess of (100 times) unlabeled ODN was used as a control. The gels were subjected to electrophoresis, dried and analyzed by autoradiography.

(5) ELISA for Determining Serum IgE Level and Tissue Histamine Level

Bloods were collected on Day 0 (before sensitization), Day 21 (before OVA challenge) and Day 24 (24 hours after last OVA challenge) and serum IgE levels were measured using ELISA (AKRIE-010, Shibayagi, Japan). Animals were sacrificed after collection of BALF and total protein was extracted from homogenized whole lung tissue. Histamine level in the protein extract (50 μg) was then measured using ELISA (EA31, Oxford Biomedical Research, Michigan).

(6) Histological and Immunohistological Studies

Animals were euthanized on Day 24 (after collection of BALF). Lower lobes of their lungs were carefully collected, fixed and then paraffin-embedded. Transverse sections (6 μm) of the lung tissues were prepared and subjected to hematoxylin-eosin (HE) staining and PAS staining.

Using VECTASTAIN Elite ABC kit, immunohistochemical staining by immunoperoxidase/avidin-biotin complex method was performed. The immune complex was identified with 0.05% 3,3'-diaminobenzidine, and nuclear staining with hematoxylin was performed. Lung frozen sections (5 μm) were stained with a rat monoclonal antibody against F4/80 (1:500, Bio-Rad) and analyzed for macrophage accumulation. IgG was used instead of the primary antibody and served as a negative control. Positively stained cells and all cells were counted and statistically analyzed.

(7) Real-Time RT-PCR

Total RNA was extracted from the lung on day 24 using RNeasy mini kit (Qiagen, Md.). SuperScript III First Strand Synthesis System (Thermo Fisher Scientific) was used to prepare the complementary DNA. Using a TaqMan probe set for Muc5ac (mucin 5AC glycoprotein) (Mm01276718-mi, Applied Biosystems, California) and a real-time PCR master mix (Toyobo Co., Ltd., Japan) and using a Prism 7900HT real-time PCR system (Applied Biosystems, California), quantitative real-time RT-PCR was performed. The expression level of GAPDH was used as an internal standard to calculate the expression of Muc5ac.

(8) Statistical Analysis

Normality was tested using Shapiro-Wilk test. A t test was used for the comparison between two groups, and a Tukey-Kramer multiple range test was used for the comparison among multiple groups. In the case of non-parametric estimation, a nonparametric Kruskal-Wallis test was used. $P<0.05$ was considered significant.

Results (1) Distribution of FITC-Labeled Decoy ODN

Figure 5:
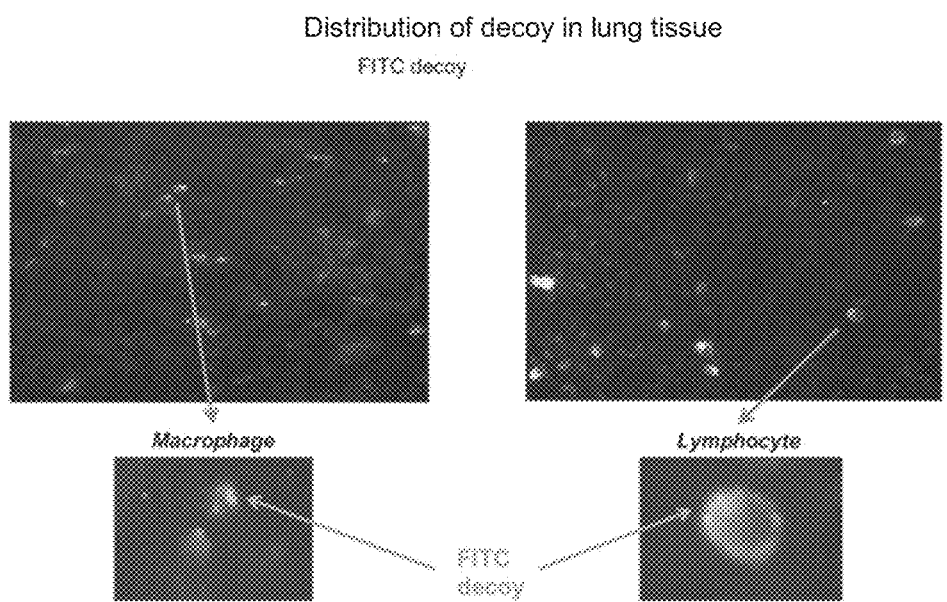
FIG. 5 shows the distribution of decoy in a lung tissue analyzed in the Examples below.

In order to confirm the introduction of decoy ODN by intratracheal administration, the distribution of fluorescein isothiocyanate (FITC)-labeled decoy ODN in an OVA-sensitized mouse was evaluated. FITC-labeled ODN was administered 3 days before OVA inhalation and histological examination showed that fluorescence could be detected mainly in lymphocytes in the alveolar space and in the peribronchial region after OVA challenge. Immunofluorescent staining revealed that FITC-labeled ODN was also detected in migrating macrophages (FIG. 5).

(2) Inhibitions of Binding Activities of NF-κB and STAT6 by Chimeric Decoy ODN

Figure 6:
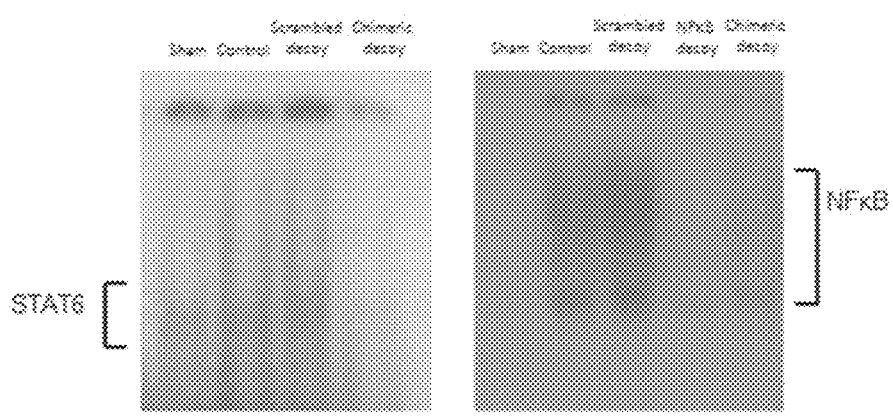
FIG. 6 depicts electropherograms showing the inhibitions of the binding activities of NF-κB and STAT6 by each chimeric decoy analyzed in the Examples below.

The inhibitory effect of chimeric decoy ODN on activation of target transcription factor was evaluated by EMSA. Activations of both NF-κB and STAT6 were markedly elevated in the nuclear extract of lungs of an OVA-sensitized mouse treated with physiological saline (control) or scrambled decoy ODN. On the other hand, activations of both NF-κB and STAT6 were markedly inhibited by introduction of chimeric decoy ODN, and activation of NF-κB was also inhibited by introduction of NF-κB decoy ODN alone (FIG. 6).

Figure 7:
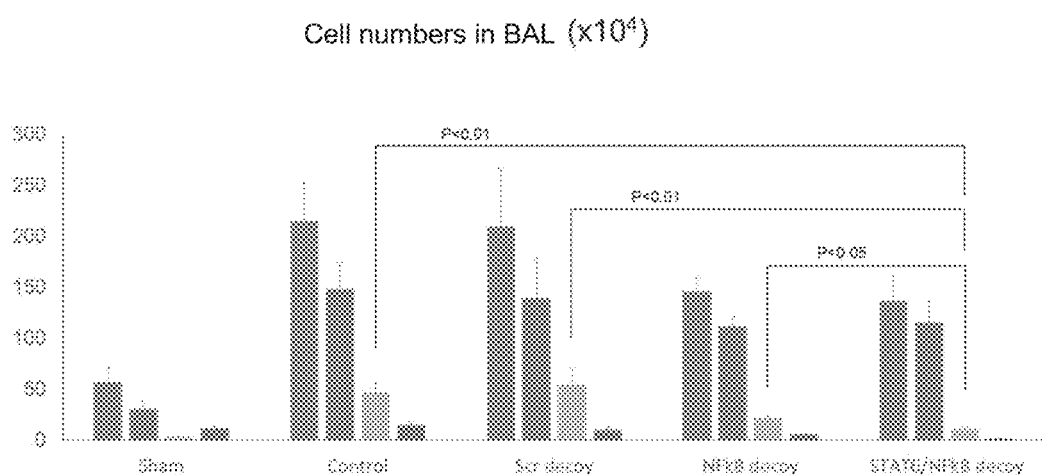
FIG. 7 shows the cell numbers of various leukocytes in a bronchoalveolar lavage (BAL) fluid after administration of various decoys as measured in the Examples below. The four histograms shown for each decoy in the figure show the number of total cells, lymphocytes, eosinophils, and neutrophils in order from the left.

(4) Inhibitions of Inflammation, Mucus Production and Histamine Secretion by Chimeric Decoy ODN To clarify the therapeutic effect of chimeric decoy ODN, we investigated the molecular mechanism of prevention of worsening of asthma. First, we evaluated the anti-inflammatory effect of chimeric decoy ODN. Total cell number in BALF increased in all treatment groups after OVA sensitization and challenge. However, in mice treated with NF-κB decoy ODN and chimeric decoy ODN, a significant decrease in eosinophil count was observed. Further, this decreasing effect of chimeric decoy ODN was significantly greater than that of NF-κB decoy ODN (FIG. 7).

Figure 8:
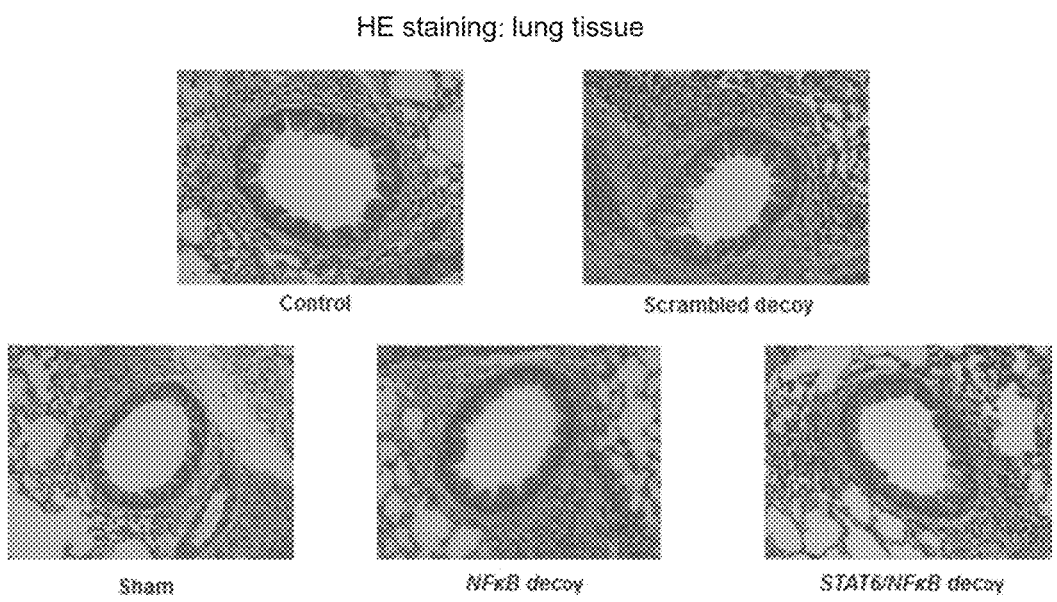
FIG. 8 shows the HE-staining results of lung tissues in each group of mouse model of OVA-induced asthma, obtained in the Examples below.
Figure 9:
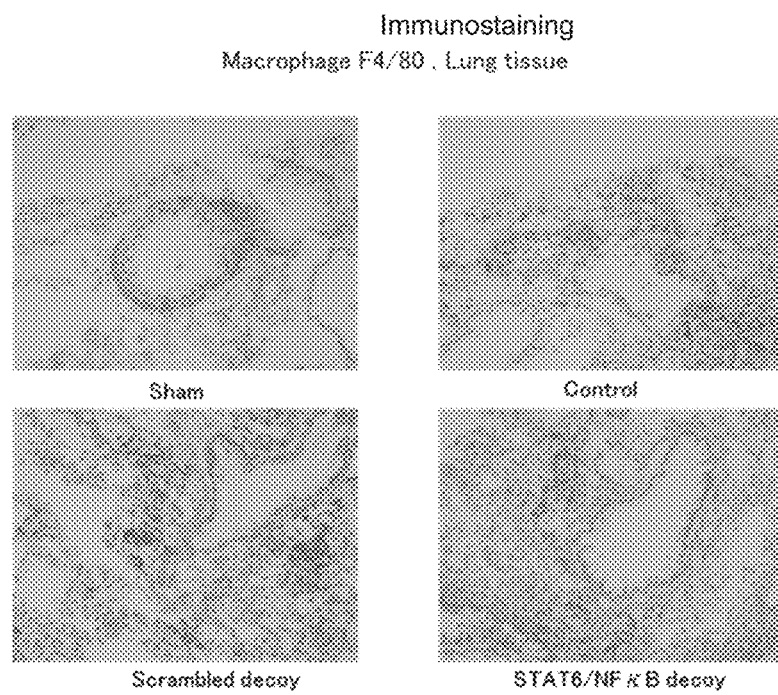
FIG. 9 shows the immunostaining results of lung tissues showing the distribution of macrophages in a mouse model of OVA-induced asthma, obtained in the Examples below.
Figure 10:
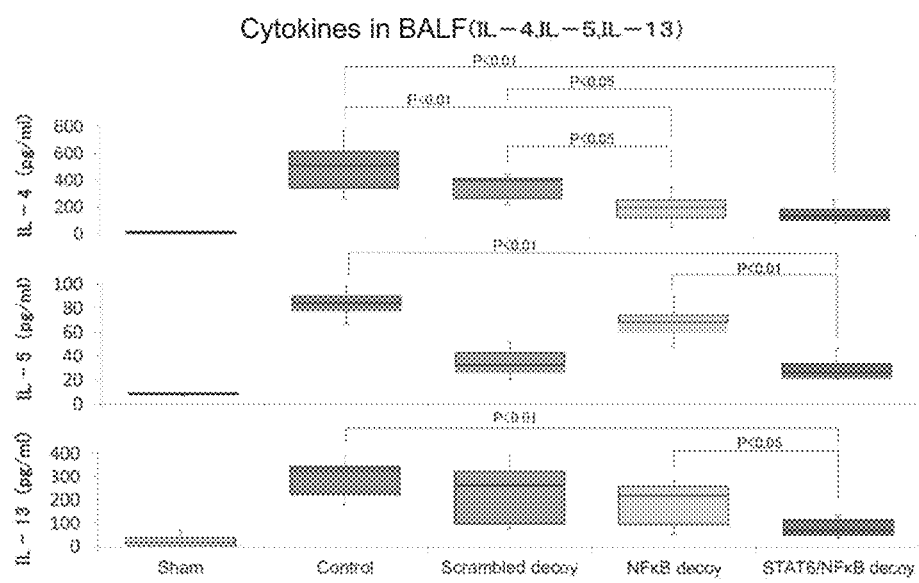
FIG. 10 shows concentrations of interleukin 4 (IL-4), interleukin 5 (IL-5) and interleukin 13 (IL-13) in a bronchoalveolar lavage fluid (BALF) after administration of various decoys as measured in the Examples below.

Histologic analysis by hematoxylin-eosin staining showed that inflammatory infiltration obviously increases in the peribronchial and perivascular regions in the control and scrambled decoy ODN groups, but recruitment of inflammatory cells are remarkably inhibited by chimeric decoy ODN (FIG. 8). Furthermore, infiltration of macrophages was inhibited by chimeric decoy ODN, while a large number of macrophages infiltrated in the peribronchial region in the group treated with scrambled decoy ODN or physiological saline (FIG. 9). Since TH2 cytokines are an important factor for the pathogenesis of allergic asthma, we further investigated these cytokines in BALF. Treatment with chimeric decoy showed remarkable inhibitions of production enhancements of IL-4, IL-5 and IL-13 in BALF. On the other hand, NF-κB decoy ODN only inhibited IL-4 secretion (FIG. 10).

Figure 11:
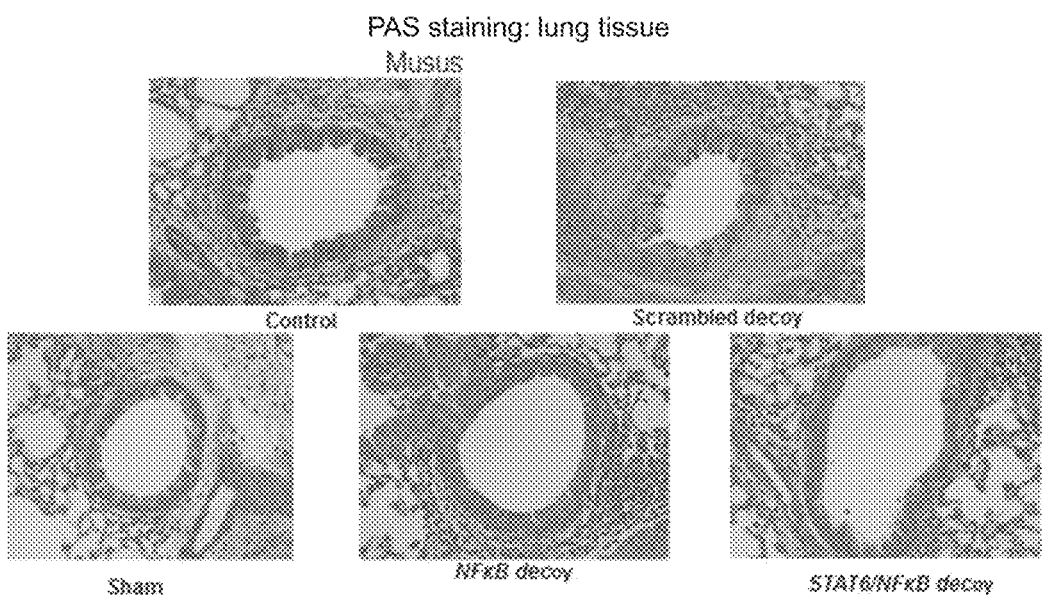
FIG. 11 shows the PAS-staining results of lung tissues in each group of mouse model of OVA-induced asthma, obtained in the Examples below.
Figure 12:
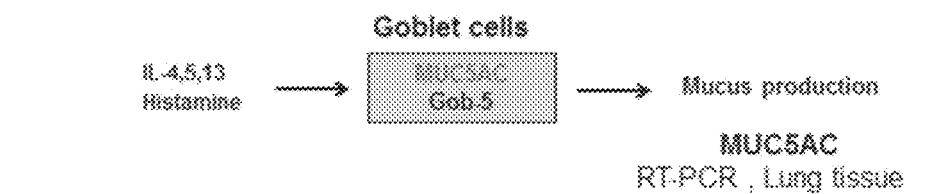
FIG. 12 is a diagram comparing the expression of mucin 5AC glycoprotein (MUC5AC) gene in each group of mouse model of OVA-induced asthma performed in the Examples below.
Figure 12:
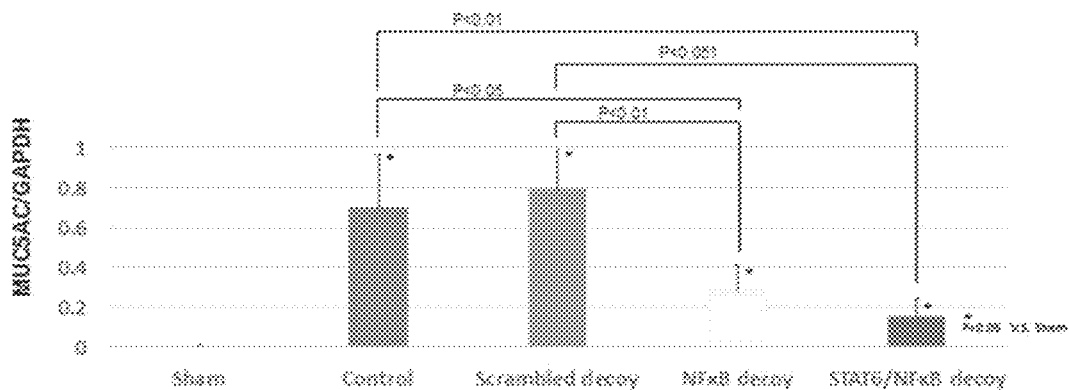

Next, since increased mucus secretion is also a major symptom of asthma, we investigated mucus production in OVA-induced asthmatic mice. In control mice and scrambled decoy ODN group, a marked increase in mucous cell numbers was shown by PAS staining (FIG. 11). However, treatment with chimeric decoy ODN markedly inhibited the increase in mucous cell numbers. Mucus production is controlled by MUC5AC. The MUC5AC gene expression was remarkably inhibited by the treatments with chimeric decoy ODN and NF-κB decoy ODN as compared with control and scrambled decoy ODN transfers (FIG. 12).

Figure 13:
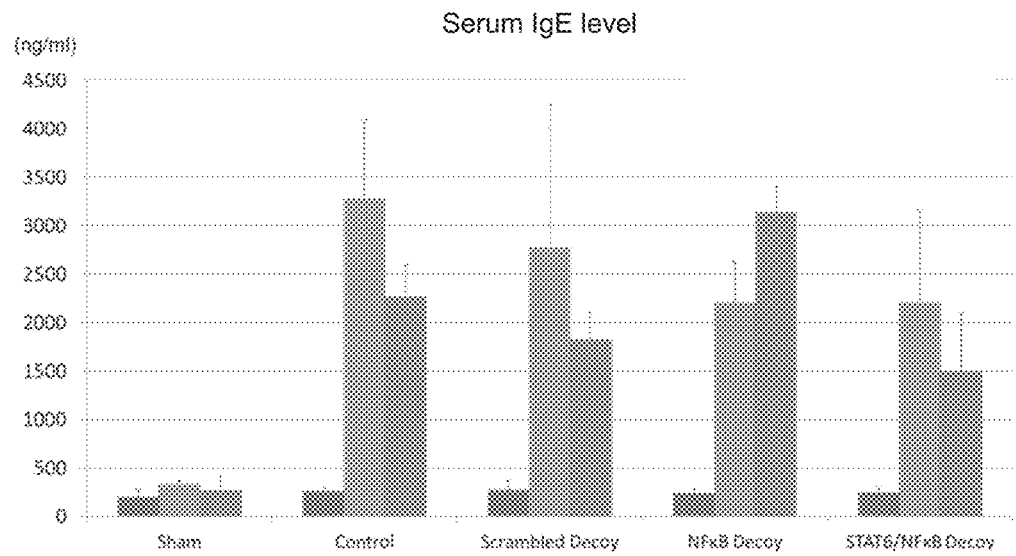
FIG. 13 shows serum IgE concentrations after administration of various decoys as measured in the Examples below. The three histograms shown for each decoy in the figure show the results of before sensitization (D0), after sensitization (D21), and after inhalation exposure (D24) in order from the left.
Figure 14:
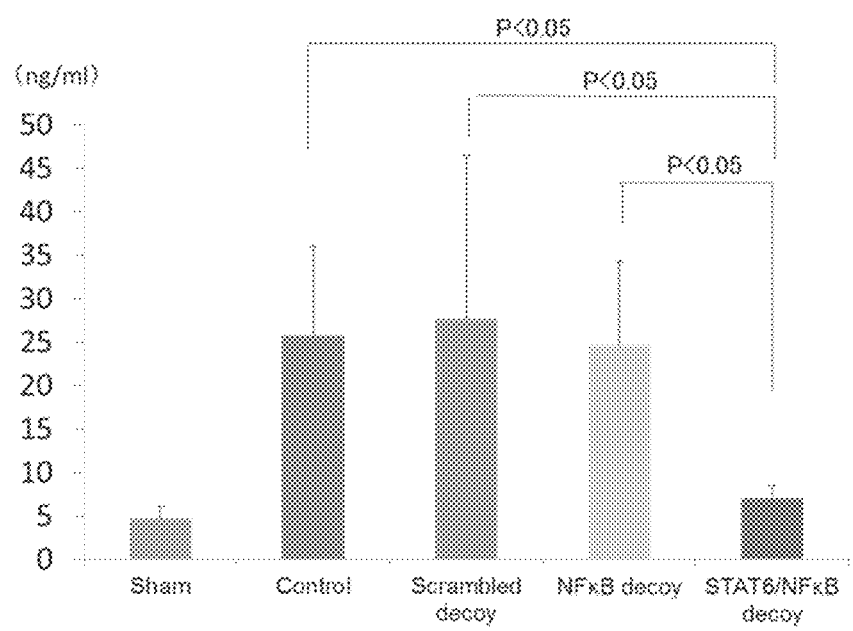
FIG. 14 shows histamine concentrations in lung tissue after administration of various decoys as measured in the Examples below.

Finally, IgE-related immune responses were investigated in this model. Serum IgE levels were elevated in all treated groups after sensitization and there was no significant difference even after OVA challenge (FIG. 13). On the other hand, the amount of histamine in lung tissue of the NF-κB decoy ODN group was almost the same as of the control group, and thus there was no effect observed, while chimeric decoy ODN showed a remarkable decreasing effect (FIG. 14).

The invention claimed is:

1. A double-stranded oligonucleotide decoy showing binding affinities for two transcription factors, comprising a first binding site for a first transcription factor and a second binding site for a second transcription factor,
wherein a first strand comprising the sense strand of said first binding site and a second strand comprising the sense strand of said second binding site are hybridized to form a double strand in which said sense strand of the first binding site and said sense strand of the second binding site are at least partly hybridized, and wherein:
said decoy has a size of 13 mer to 15 mer and is a hairpin double strand.

2. The decoy according to claim 1, wherein at least one of the binding sites has one single base substitution in a consensus sequence of each transcription factor binding site.

3. The decoy according to claim 1, wherein said first and second transcription factors are two different transcription factors, and wherein the two different transcription factors are selected from the following combinations (1) to (5):
(1) NF-κB and Ets1;
(2) NF-κB and NF-AT;
(3) NF-κB and STAT1;
(4) NF-κB and STAT6; and
(5) NF-κB and NF-IL6.

4. The decoy according to claim 3, wherein said two different transcription factors are NF-κB and STAT6.

5. The decoy according to claim 3, wherein the decoy comprises a sequence selected from the group consisting of SEQ ID NO: 1, 6, 7, 8, 9, 10, 11, 12, 13 and 14.

6. The decoy according to claim 4, wherein the decoy comprises the sequence of SEQ ID NO: 1.

7. The decoy according to claim 1, having a size of 15 mer.

8. A double-stranded oligonucleotide decoy showing binding affinities for two transcription factors, comprising a first binding site for a first transcription factor and a second binding site for a second transcription factor,
wherein a first strand comprising the sense strand of said first binding site and a second strand comprising the sense strand of said second binding site are hybridized to form a double strand in which said sense strand of the first binding site and said sense strand of the second binding site are at least partly hybridized,
wherein said decoy has a size of 13 mer to 15 mer, and
wherein at least a part of bonds between each nucleotide in the double-stranded oligonucleotide constituting the decoy includes a phosphorothioate bond.

9. A double-stranded oligonucleotide decoy showing binding affinities for two transcription factors, comprising a first binding site for a first transcription factor and a second binding site for a second transcription factor,
wherein a first strand comprising the sense strand of said first binding site and a second strand comprising the sense strand of said second binding site are hybridized to form a double strand in which said sense strand of the first binding site and said sense strand of the second binding site are at least partly hybridized,
wherein said decoy has a size of 13 mer to 15 mer, and
wherein the decoy has a 5' end, and wherein the 5' end of the decoy is bound, via a linker or directly, to a polylactic acid/glycolic acid copolymer (PLGA) nanoparticle.

* * * * *